United States Patent
Friedman et al.

[11] Patent Number: 5,993,396
[45] Date of Patent: Nov. 30, 1999

[54] METHOD AND APPARATUS FOR DETERMINING A MINIMUM WAIT TIME BETWEEN BLOOD PRESSURE DETERMINATIONS

[75] Inventors: Bruce Friedman, Tampa; Richard Avoy, Palm Harbor; Richard Medero, Tampa, all of Fla.

[73] Assignee: Critikon Company, L.L.C., Tampa, Fla.

[21] Appl. No.: 09/021,869

[22] Filed: Feb. 11, 1998

[51] Int. Cl.⁶ .................................................. A61N 5/00
[52] U.S. Cl. ........................... 600/490; 600/481; 600/500
[58] Field of Search ...................... 600/479–500

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/681 |
| 4,638,810 | 1/1987 | Ramsey, III et al. | 128/681 |
| 4,754,761 | 7/1988 | Ramsey, III et al. | 128/683 |
| 4,889,133 | 12/1989 | Nelson et al. | 128/681 |
| 4,949,710 | 8/1990 | Dorsett et al. | 128/680 |
| 4,967,757 | 11/1990 | Frankenreiter | 128/682 |
| 5,052,397 | 10/1991 | Ramsey, III et al. | 128/682 |
| 5,170,795 | 12/1992 | Ramsey, III et al. | 128/682 |
| 5,590,662 | 1/1997 | Hersh et al. | 600/494 |
| 5,606,977 | 3/1997 | Ramsey, III et al. | 128/680 |

*Primary Examiner*—Cary O'Connor
*Assistant Examiner*—Michael Astorino
*Attorney, Agent, or Firm*—Woodcock Washburn Kurtz Mackiewicz & Norris LLP

[57] ABSTRACT

An automated non-invasive blood pressure (NIBP) monitor having a stat mode of operation wherein several cycles of blood pressure measurement are undertaken in rapid succession by inflating a cuff on an appendage of the patient in order to quickly provide a clinician with readings of blood pressure and pulse rate. The NIBP monitor adaptively determines a minimum wait time between stat mode blood pressure measurement cycles by recognizing that the minimum wait time is proportional to the area under the pressure-time curve of the previous inflation/deflation measurement cycle. The calculated area is divided by a clinical constant derived from sampled patient data to determine the minimum wait time. The minimum wait time between blood measurement cycles so determined allows for venous return of blood that has accumulated in a patient's extremity and minimizes the discomfort experienced by the patient while maximizing the amount of collected data.

34 Claims, 4 Drawing Sheets

METHOD AND APPARATUS FOR DETERMINING A MINIMUM WAIT TIME BETWEEN BLOOD PRESSURE DETERMINATIONS

FIELD OF THE INVENTION

This invention relates to automated blood pressure monitoring, and more particularly, to automated blood pressure monitors that utilize a pneumatic cuff for accomplishing successive sphygmomanometric measurements on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith, employs the oscillometric methodology. In accordance with the Ramsey patents, an inflatable cuff is suitably located on the limb of a patient and is pumped up to a predetermined pressure above the systolic pressure. The cuff pressure is then reduced in predetermined steps to a pressure below diastolic pressure, and at each step, pressure oscillations are monitored. On the other hand, the pressure may be reduced linearly or exponentially to a pressure below diastolic pressure before the pressure is exhausted to a near-zero pressure. The resultant signals typically consist of a DC voltage with a small superimposed variational component caused by arterial blood pressure pulsations (referred to herein as "heart cycles," "oscillation complexes" or just simply "oscillations"). After suitable filtering to reject the DC component and to provide amplification, peak pulse amplitudes (PPA) above a given baseline are measured and stored. As the decrementing of cuff pressure continues, the peak pulse amplitudes will normally increase from a lower level to a relative maximum, and thereafter will decrease. These amplitudes thus form an oscillometric blood pressure envelope for the patient. The cuff pressure at which the oscillations have a maximum value has been found to be representative of the mean arterial pressure ("MAP"). Systolic and diastolic pressures can be derived either as predetermined fractions of MAP, or by more sophisticated methods of direct processing of the oscillation complexes.

The step deflation technique as set forth in the Ramsey patents is the commercial standard of operation. A large percentage of clinically acceptable automated non-invasive blood pressure monitors ("NIBP") utilize the step deflation method. When in use, the blood pressure cuff is placed on the patient and the operator sets a time interval at which blood pressure measurements (i.e., cuff inflations) are to be made. The non-invasive blood pressure monitor automatically starts a blood pressure determination at the end of the set time interval. Typically, the user selects a short interval if the patient is unstable (since blood pressure may change to dangerous levels in a short time) and selects a longer interval as the patient becomes more stable.

In those situations where a short time interval is necessary, for example, in the so-called "stat mode," several cycles of blood pressure determinations are performed in rapid succession over a period of time such as five minutes. The stat mode of operation is utilized to rapidly track blood pressure, as when a patient is unstable and changes in the patent's blood pressure must be quickly detected and medical personnel alerted, if necessary. The clinician's need in stat mode is for as many readings of blood pressure and pulse rate as possible, as quickly as possible. This need must be balanced against some minimum time between cuff inflations (wait time) which is need to allow for circulation to the extremity distal from the cuff and to allow for venous blood to return from the extremity. In addition, any discomfort experienced by the patient while having cuff pressure on his or her limb for an extended period of time must be minimized.

Typically, these considerations are addressed in conventional systems by using a fixed interval between measurement cycles in the stat mode of operation. For example, the measurement cycle begins 3 seconds after the cuff pressure in the current cycle has fallen below 10 mm Hg. However, this approach does not account for the physiological minimum wait time between cuff inflation cycles which is necessary to allow venous blood flow to return from the distal end of the limb in order to minimize venous pooling. Thus, in the stat mode of operation, if the wait time is too short, the patient will experience pain and discomfort due to the reduced circulation. On the other hand, if the wait time is too long, dangerous changes in pressure may go undetected, which could lead to disastrous results if it is wrongly assumed that the patient's blood pressure is stable.

An example of a convention blood pressure measuring apparatus having a stat mode of operation may be found in U.S. Pat. No. 4,967,757, to Frankenreiter. The blood pressure measuring device of Frankenreiter determines a patient's blood pressure by inflating a cuff to a pressure $P_{max}$ above the systolic pressure to occlude an artery within the patent's limb. The cuff pressure is incrementally reduced to a pressure $P_{min}$ below the diastolic pressure. A time $t_{next}$ to begin a next blood pressure measurement is determined as a function of the time required to perform the present measurement cycle. In particular, Frankenreiter discloses a first time interval $\Delta t_{pre}$ in a measurement cycle that begins after the cuff pressure reaches a threshold pressure $P_{thr}$, (e.g., MAP), during inflation. The time interval $\Delta t_{pre}$ ends when the cuff pressure reaches the threshold pressure $P_{thr}$ during the cuff deflation sequence. A second time interval $\Delta t_{preII}$, which is equal to $\Delta t_{pre}$, begins immediately after the cuff pressure reaches $P_{thr}$. After time period $\Delta t_{preII}$ expires, the next cuff inflation cycle begins. According to Frankenreiter, the total time period of $\Delta t_{pre}$ and $\Delta t_{preII}$ provides for a dead time $t_{dea}$ between measurement cycles. However, Frankenreiter describes situations where the total time period of $\Delta t_{pre}$ and $\Delta t_{preII}$ fails to yield the proper wait time. For example, a predetermined minimum wait time $\Delta t_{min}$ is used if the cuff pressure is greater than $P_{min}$ upon the expiration of $\Delta t_{preII}$. In addition, a predetermined maximum wait time period $\Delta t_{max}$ is used if the time period $\Delta t_{pre}$ should be unusually long. Thus, while under most circumstances the Frankenreiter system determines a wait time between measurement cycles, there are circumstances where operator-entered default time periods are used, which may not be a proper time period to allow for venous blood that has accumulated in a patient's extremity to return, nor properly provide for patient comfort and safety.

Another example of a blood pressure measurement apparatus is described in U.S. Pat. No. 4,889,133, to Nelson et al. The Nelson et al. apparatus raises the cuff pressure to a level above the systolic pressure and decreases the cuff pressure in a step-wise manner to an ending pressure which is less that the diastolic pressure. Pulsations due to heart contractions are detected at each of the decreasing cuff pressures. An impulse value, which is related to the detected pulsations, is determined from the area under the pressure waveform up to the maximum pulsation amplitude at each cuff pressure. The MAP is determined from the lowest cuff pressure having the largest waveform area (i.e., impulse area,). In addition, a prediction curve is initially generated from the first two impulse values and smoothed by subsequent impulse values in order to predict the next impulse value, reject invalid readings, and form a final smoothed curve. From the final curve, blood pressure parameters such as the systolic and diastolic pressure may be derived and displayed. While Nelson et al. discloses a technique whereby the area of the pressure waveform is utilized, the Nelson et al. technique fails to directly address the Stat mode of operation, nor does Nelson et al. address determining a waiting period between monitoring cycles.

Yet another example of a NIBP measurement apparatus is that of U.S. Pat. No. 5,606,977, to Ramsey, III et al., which is commonly assigned herewith. Ramsey discloses a blood pressure monitoring device that makes a complete determination of a patient's blood pressure at user-specified intervals. At the end of the user-specified interval, an inflatable cuff is pumped up to a pressure above the systolic pressure. The cuff is then incrementally deflated, and at each level, pressure fluctuations are monitored to form an oscillometric blood pressure envelope which is stored by the monitoring device. Between the user-specified intervals, the device is periodically inflated to a check pressure below the mean arterial pressure ("MAP"), and certain points on the patient's oscillometric envelope at the check pressure are compared to the stored oscillometric envelope derived from the previous complete blood pressure determination. If the signals from the check pressure determination differ by a predetermined amount from the stored signals, it is determined that the patient's blood pressure has changed significantly and that a complete blood pressure determination should be initiated immediately (i.e., before the expiration of a user-specified time interval). Otherwise, further check inflates are performed until the user-specified time period expires or it is otherwise determined that a complete inflate cycle should be conducted. According to Ramsey, inflations to the check pressure in this so-called "guard mode" of operation are conducted at a cycle time which is 1/50 that of the user-specified time period for a complete blood pressure determination, and are performed in addition to the complete determinations that occur at the end of the user-specified time period. While the check inflate sequence in the "guard mode" reduces the amount of trauma caused to the patient's limb as compared to a complete blood pressure determination, the "guard mode" sequence does not repeatedly collect data to establish a baseline as in the stat mode of operation. In any case, in the guard mode, the time between cycles is set by the operator and is not related to the time needed for venous return flow.

It is, accordingly, an object of the present invention to provide a system which automatically determines a minimum wait time between cuff inflations of blood pressure monitoring sequences. It is also an object of the invention to provide a system that adapts the wait time to minimize the level of patient discomfort by minimizing venous pooling. It is also an object of the present invention to provide a technique for monitoring the status of the patient's blood pressure which provides for faster blood pressure updates, thus increasing patient safety.

SUMMARY OF THE INVENTION

The above objects have been met in accordance with the present invention by providing an automated sphygmomanometer which monitors a patient's blood pressure at very short intervals while in the so-called stat mode of operation and provides a variable wait time between stat mode determinations. In a preferred embodiment, the calculated wait time varies in proportion to the area under the pressure-time curve of the previous inflation, which provides a good indication of patient discomfort. Adjusting the wait time in proportion to the area under the pressure-time curve allows the appropriate time for patient recovery from the discomfort of the cuff pressure and any venous pooling, while maximizing the amount of available data.

The present invention relates to an automated sphygmomanometer apparatus comprising an inflatable pressure cuff, means to inflate the cuff, an inflation valve which controls the inflation of the cuff to pressurize the cuff to a predetermined pressure, a pressure transducer which senses cuff pressure and produces a cuff pressure determination signal representative of a sensed cuff pressure, a deflation valve which selectively deflates the cuff to relieve pressure within the cuff, and a controller which controls the inflation and deflation cycles of the cuff at predetermined intervals in accordance with the cuff pressure determination signal. The controller determines a wait time between the end of one deflation cycle and the beginning of a subsequent inflation cycle after the deflation valve deflates the cuff to a pressure below a predetermined minimum pressure by dividing an area under a pressure versus time curve by an empirically derived clinical constant selected to minimize patient discomfort. However, if the calculated wait time is less than a predetermined value, the wait time is set to a predetermined minimum wait time, such as 2 seconds.

In accordance with a feature of the present invention, the pressure transducer further senses any blood pressure oscillations in the cuff pressure and produces an output representative of the blood pressure oscillations of the patient. From the oscillations, the controller determines a systolic pressure of the patient being monitored. The controller then determines an area under a curve representative of systolic pressure minus cuff pressure versus the number of heart cycles. The area is divided by the clinical constant to determine the wait time. However, if the calculated wait time is less than a predetermined value, the wait time is set to the predetermined minimum wait time.

In accordance with another aspect of the present invention, a method of determining a minimum wait time between blood pressure determinations using an automated sphygmomanometer apparatus having an inflatable pressure cuff is provided in which the area under a cuff pressure versus time curve is used to determine the minimum wait time. The method comprises the steps of inflating the cuff to pressurize the cuff; sensing cuff pressure and producing a cuff pressure determination signal representative of a sensed cuff pressure; receiving the cuff pressure determination signal and periodically storing the sensed cuff pressure; selectively deflating the cuff to relieve pressure within the cuff; and determining a wait time between cycles of the automated sphygmomanometer based on an area under a cuff pressure versus time curve divided by a clinical constant. The calculated wait time may be compared with a predetermined minimum wait time, and if the wait time is less than the predetermined minimum, the wait time is set to the predetermined minimum wait time.

In accordance with the inventive method, blood pressure oscillations in the detected cuff pressure are detected and an output representative of the blood pressure oscillations of the patient is produced. The patient's systolic pressure is determined based on the output. From that, an area under a curve of systolic pressure minus cuff pressure versus a number of heart cycles is determined. The area is divided by a clinical constant to determined the wait time. However, if the wait time is less than the predetermined minimum wait time, the wait time is set to the predetermined minimum wait time.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PREFERRED EMBODIMENTS

A system and method which meets the above-mentioned objects and provides other beneficial features in accordance with the presently preferred exemplary embodiment of the invention will be described below with reference to FIGS. 1–4. Those skilled in the art will readily appreciate that the description given herein with respect to those figures is for explanatory purposes only and is not intended in any way to limit the scope of the invention.

In U.S. Pat. No. 4,360,029, Ramsey discloses in great detail a system for oscillometric blood pressure monitoring to which the principles of the present invention may be applied with advantage. The disclosure of the commonly assigned Ramsey '029 patent is incorporated by reference herein. The following description of FIG. 1 will act as a brief summary of the operation of that system.

Figure 1:
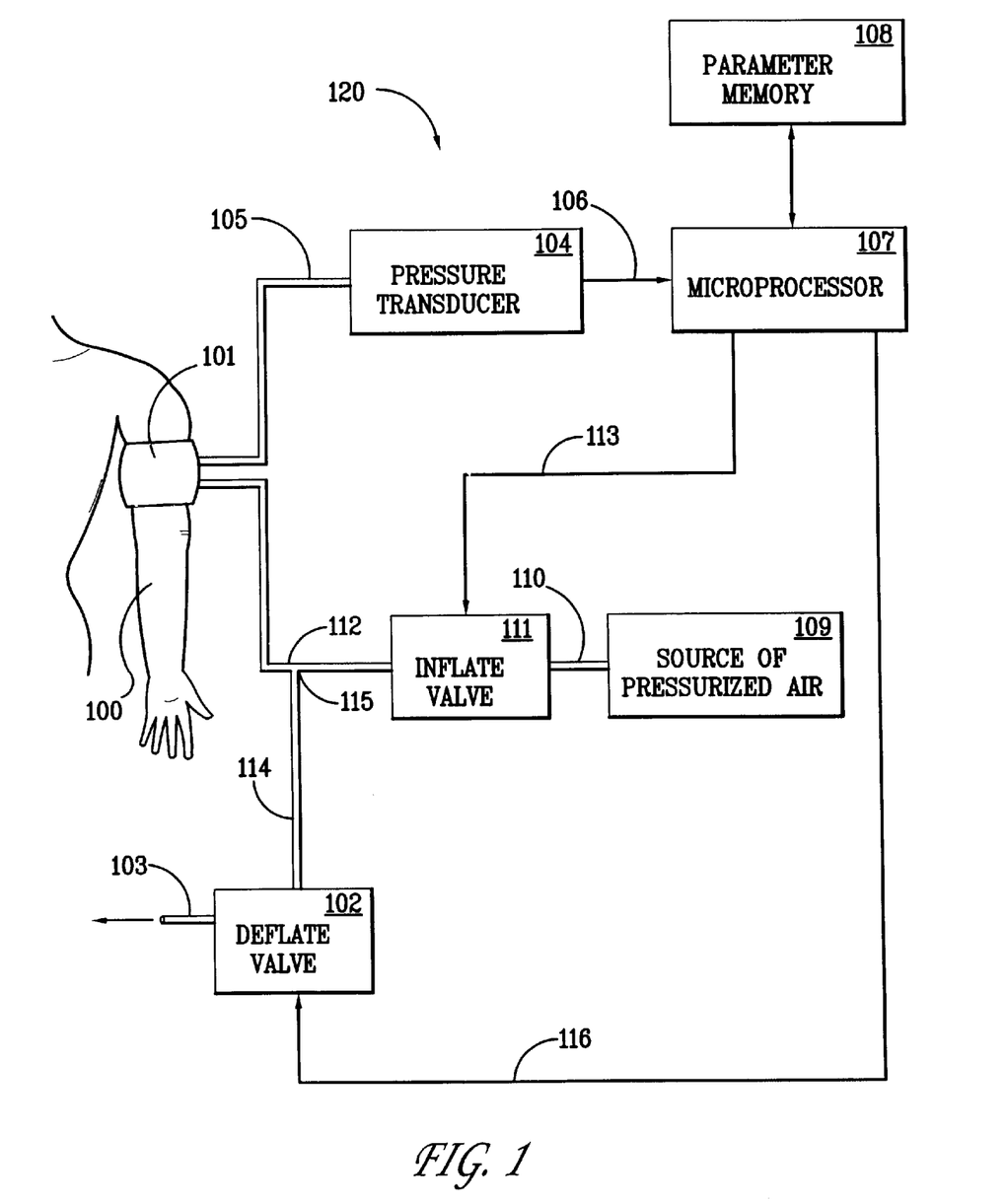
FIG. 1 is a schematic representation of a non-invasive blood pressure ("NIBP") monitor embodying the present invention.

In FIG. 1, the arm 100 of a human subject is shown wearing a conventional flexible inflatable and a deflatable cuff 101 operatively coupled to a NIBP monitor 120 for occluding the brachial artery when fully inflated. As the cuff 101 is deflated using a deflate valve 102 having an exhaust 103, the arterial occlusion is gradually relieved. As will be described more fully below, the deflation of cuff 101 via the deflate valve 102 is controlled by a microprocessor 107 via a control line 116.

A pressure transducer 104 is coupled by a duct 105 to the cuff 101 for sensing the pressure therein. In accordance with conventional oscillometric techniques, pressure oscillations in the artery caused by contractions of the heart are sensed by changes in the counter-pressure of the cuff 101, and these pressure oscillations are converted into an electrical signal by the transducer 104 and coupled over a path 106 to the microprocessor 107 for processing. In addition, a source of pressurized air or pump 109 is connected via a duct 110 through an inflate valve 111 and a duct 112 to the pressure cuff 101. The inflate valve 111 is electrically controlled through a path 113 from the microprocessor 107. Also, the deflate valve 102 is connected by a duct 114 via a branch connection 1 15 with the duct 112 leading to the cuff 101. A parameter memory 108 is also provided for storing parameters such as envelope shape and size, systolic pressure, diastolic pressure, oscillation shape at diastolic, data points on a pressure versus time curve (i.e., the oscillometric blood pressure envelope), and the pulse period representative of the information gathered during each NIBP determination. As would be apparent to one of skill in the art, the parameter memory 108 may be utilized to store additional information related to the measurement of a patient's blood pressure.

From the standpoint of the principles of the present invention, the processing of the signals from the pressure transducer 104 by the microprocessor 107 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al. in U.S. Pat. No. 4,543,962, of Medero in U.S. Pat. No. 4,546,775, of Hood, Jr. et al. in U.S. Pat. No. 4,461,266, of Ramsey, III et al. in U.S. Pat. No. 4,638,810, of Ramsey, III et al. in U.S. Pat. No. 4,754,761, of Ramsey, III et al. in U.S. Pat. No. 5,170,795, and of Ramsey, III et al. in U.S. Pat. No. 5,052,397, all of which are commonly assigned herewith and the disclosures of which are hereby incorporated by reference. In any event, it is desirable to use any of the known techniques to determine the quality of the oscillation complexes received at each level so that the blood pressure determination is made using actual blood pressure data and not artifacts.

The apparatus described above with reference to FIG. 1, except for the programming of the microprocessor 107, can be substantially the same as that disclosed in the Ramsey, III et al. '029 and '034 patents. Thus, during operation of the apparatus illustrated in FIG. 1, it can be assumed that air under pressure to about 8–10 p.s.i. is available in the source of pressurized air 109. When it is desired to initiate a determination of blood pressure, the microprocessor 107 furnishes a signal over the path 113 to open the inflate valve 111. The deflate valve 102 is closed. Air from the source 109 is passed through the inflate valve 111 and the duct 112 to inflate the cuff 101 to a desired level, preferably above the estimated systolic pressure of the patient. The microprocessor 107 responds to a signal on the path 106 from the pressure transducer 104, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over the path 113 instructing the inflate valve 111 to close. Once the inflate valve 111 has been closed, the blood pressure measurement can be obtained by commencing the deflate routine.

As noted above, actual measurement of the blood pressure under the control of the microprocessor 107 and the deflate valve 102 as sensed by the pressure transducer 104 can be accomplished in any suitable manner such as that disclosed in the aforementioned patents. At the completion of each measurement cycle, the deflate valve 102 can be re-opened long enough to relax the cuff pressure substantially completely via the exhaust 103. Thereafter, the deflate valve 102 is closed for the start of a new measurement cycle.

By way of a summation, when a blood pressure measurement is desired, the inflate valve 111 is opened while the cuff pressure is supervised by the pressure transducer 104 until the cuff pressure reaches the desired level. The inflate valve 111 is then closed. Thereafter, the deflate valve 102 is operated using a signal 116 from the microprocessor 107 and the blood pressure measurement taken. To this point, the monitor operates in a conventional manner. The present invention relates to a technique which automatically determines the minimum wait time between such measurement cycles independent of the set wait time for NIBP determinations.

Figure 2:
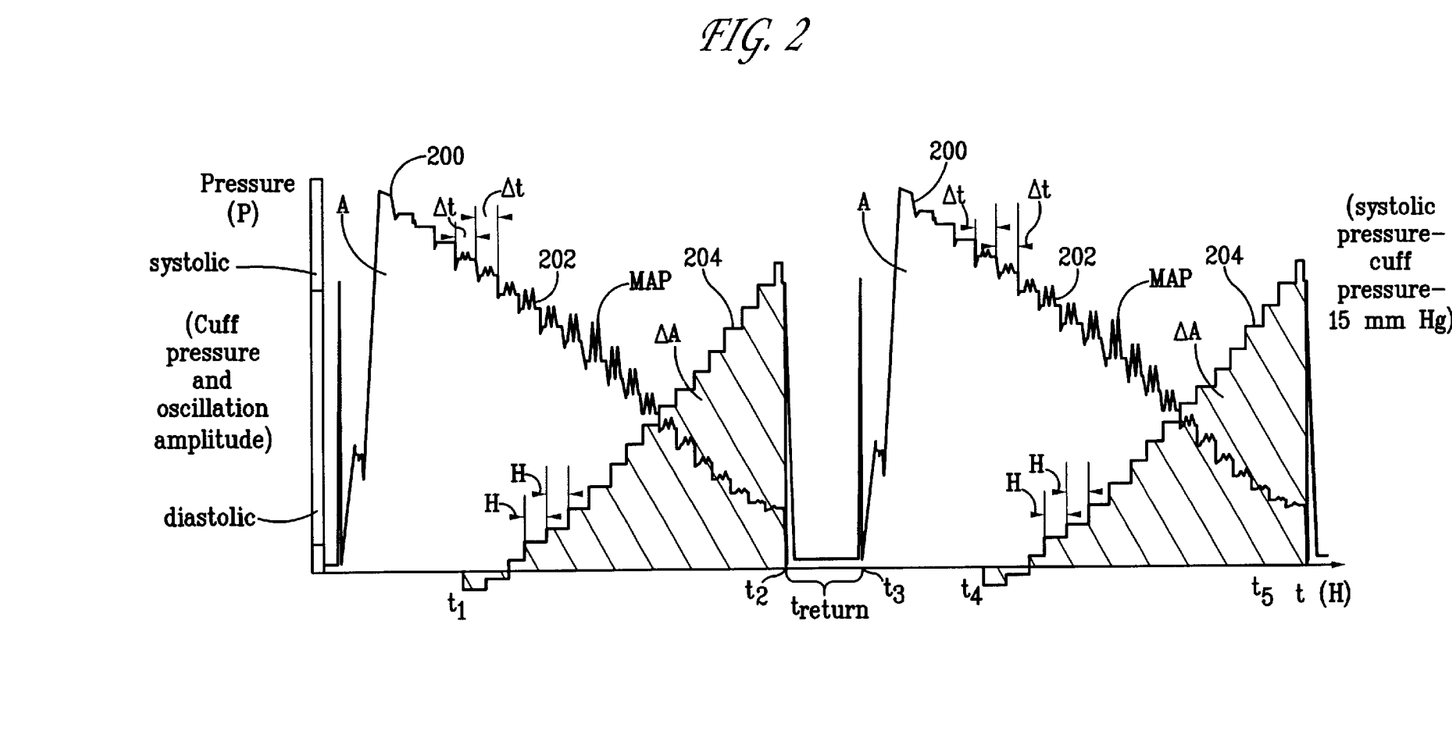
FIG. 2 is an exemplary pressure versus time graph illustrating a plurality of measurement cycles including step deflation steps and the corresponding oscillation complexes measured using a NIBP monitor and exemplary graphs of the difference between systolic pressure and cuff pressure.

In automatic sphygmomanometric devices, the cuff deflation operation is accomplished in equal decrements of approximately 8 mm Hg per step. FIG. 2 illustrates exemplary pressure versus time graphs 200 illustrating two cuff step deflation and measurement cycles (NIBP measurement cycle) of the NIBP monitor 120. The graphs 200 represents the pressure of the cuff 101, which is inflated to a pressure above the systolic pressure, and then deflated in steps of equal duration at about 8 mm Hg per step. A timeout duration $\Delta t$ is provided at each step during which the signal processing circuitry searches for oscillation complexes 202 in accordance with the techniques described in the aforementioned commonly assigned patents. At the end of timeout duration $\Delta t$, the cuff pressure is decremented even if no oscillation complex is detected.

As will be described below, the present invention adaptively determines a minimum waiting time $t_{return}$ between the end of a NIBP monitoring cycle (at time $t_2$) and the beginning of a subsequent NIBP monitoring cycle (at time $t_3$). The minimum wait time $t_{return}$ is determined so as to allow for venous return of blood that may have accumulated in an extremity during the measurement cycle. Blood accumulates in the extremities because the patient's circulation is reduced by the pressure exerted on the patient's limb 100 by the cuff 101. Typically, the blood accumulation, caused by the so-called venous pooling, occurs when the cuff pressure is higher than 15 mm Hg. As will be described below in greater detail with respect to FIG. 3, the area under the cuff pressure versus time curve 200 may be utilized in the determination of a minimum wait time $t_{return}$ between NIBP monitoring cycles. In accordance with another embodiment described with respect to FIG. 4, the area under a curve 204 representative of systolic pressure minus cuff pressure minus 15 mm Hg versus a number of heart cycles is utilized in the determination of the minimum wait time $t_{return}$ between NIBP monitoring cycles.

Figure 3:
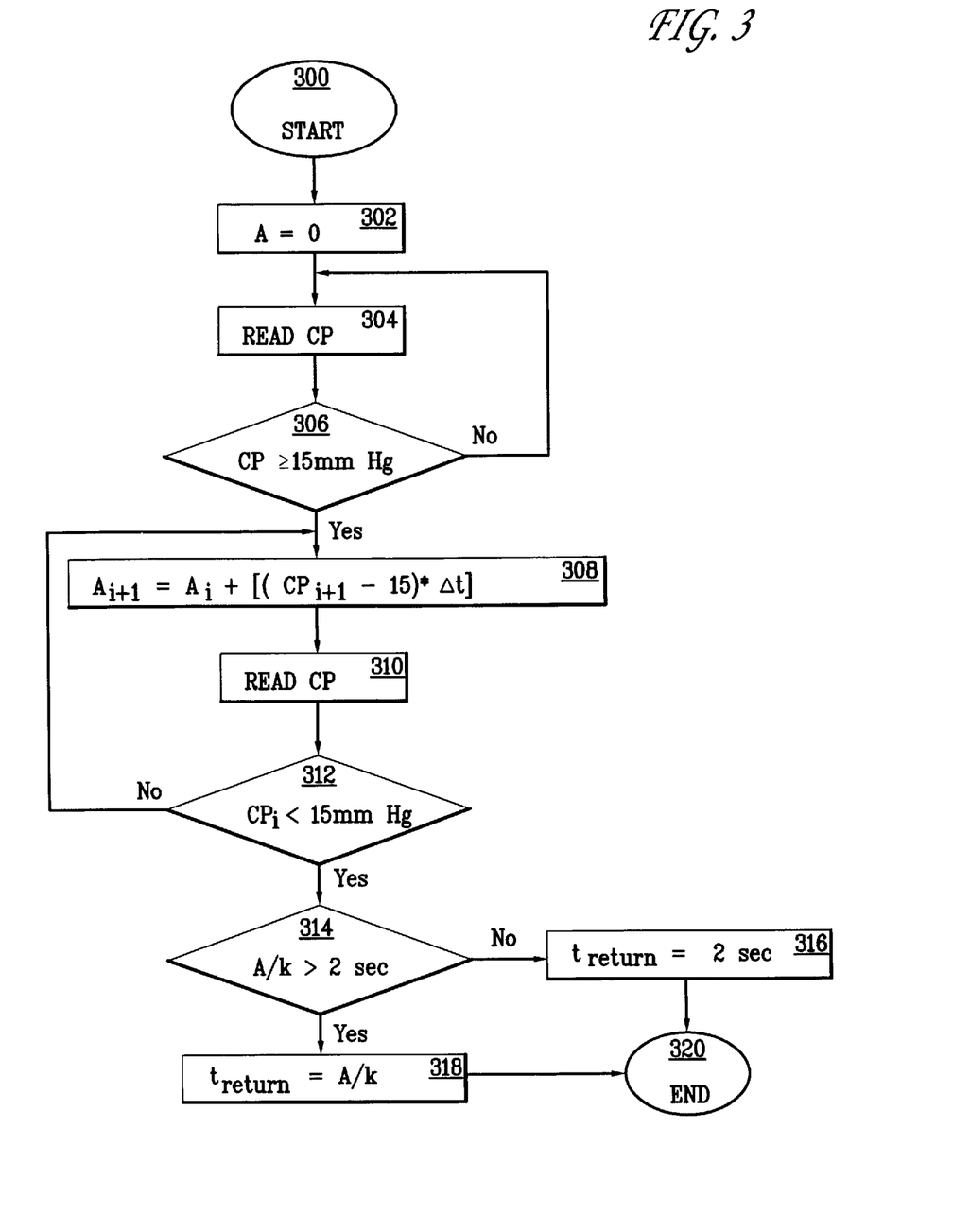
FIG. 3 is a flow chart representing the processes performed to determine a minimum waiting period during a Stat mode of operation in accordance with an embodiment of the present invention.

Referring now to FIG. 3, there is illustrated a flow chart of the processes performed to determine a minimum wait time $t_{return}$ in accordance with a first embodiment of the present invention wherein the entire area under the NIBP envelope is used. The processes of FIG. 3 may be written in a suitable programming language and executed by the microprocessor 107 during operation of the NIBP monitor 120. As will be described, the embodiment of FIG. 3 utilizes the total area A under the pressure versus time curve 200 for a previous inflation to determine the minimum wait time $t_{return}$ between blood pressure determination cycles.

At step 300 the process to determine the minimum wait time interval $t_{return}$ begins. At step 302, the calculated total area A under the cuff pressure curve 200 is initialized and set to zero. At step 304 the first cuff pressure CP in the previous NIBP determination is read. As noted above, the cuff pressure CP is determined based on an output of the pressure transducer 104. At step 306, it is determined if the cuff pressure CP is greater than or equal to 15 mm Hg, which is selected because venous pooling begins at this pressure. If the cuff pressure CP is not greater than or equal to 15 mm Hg, then the process returns to step 304 to read another cuff pressure CP.

If at step 306 it is determined that the cuff pressure CP is greater than or equal to 15 mm Hg, then the running total area A under the cuff pressure-time curve for the previous NIBP determination is updated at step 308 by multiplying the venous pooling pressure (above 15 mm Hg) by the time at that cuff pressure as follows:

$$A_{i+1} = A_i + ((CP_{i+1} - 15) * \Delta t)$$

where:

$A_i$=Total area under the pressure-time curve at time i;
$CP_i$=Cuff pressure at the pressure step at time i; and
$\Delta t$=Duration of time at pressure step at time i.

At step 310 the next cuff pressure CP in the previous NIBP determination is read, and at step 312 it is determined if the cuff pressure CP is less than 15 mm Hg. If the cuff pressure CP is not less than 15 mm Hg, then the process returns to step 308 to recalculate the total area under the pressure-time curve in view of the new CP data. If the cuff pressure CP is less than 15 mm Hg (e.g., at time $t_2$ in FIG. 2), then at step 314 the total area A under the cuff pressure curve 200 is divided by a clinical constant k to determine the minimum wait time $t_{return}$. The clinical constant k is empirically derived from results of clinical testing and sampled data, and correlates the area A to a wait time $t_{return}$ such that venous pooling effects for the typical patient are minimized. If the result of step 314 is greater than 2 seconds, then at step 318 the wait time $t_{return}$ is set to the calculated value determined at step 314. If, however, the calculated wait time $t_{return}$ is determined not to be greater than 2 seconds, then the wait time is set to a minimum wait time, e.g., 2 seconds, at step 316. After the minimum wait time $t_{return}$ is set at step 316 or 318, then the process for the current measurement cycle ends at step 320.

Figure 4:
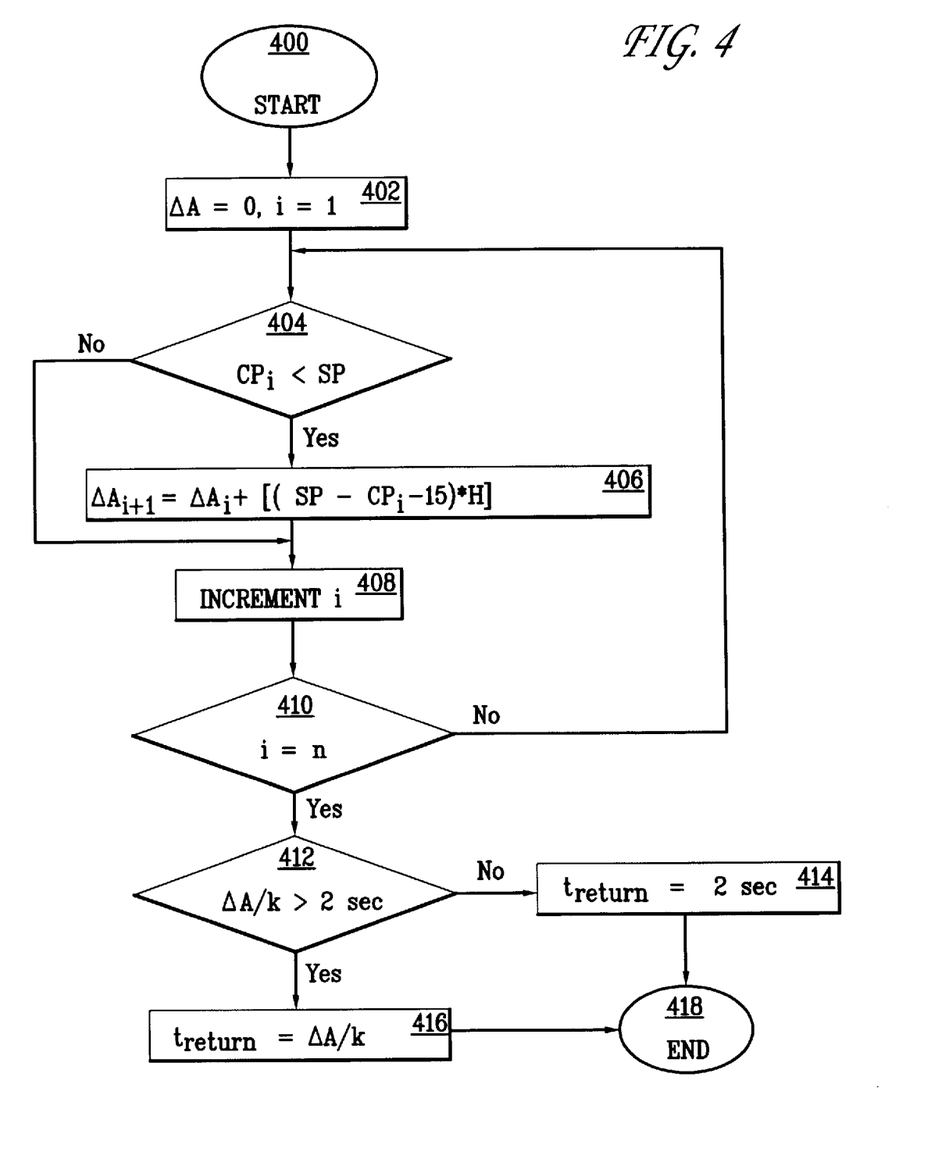
FIG. 4 is a flow chart representing the processes performed to determine a minimum waiting period during a Stat mode of operation in accordance with another embodiment of the present invention.

FIG. 4 is a flow chart of the processes performed to determine a minimum wait time $t_{return}$ in accordance with another embodiment of the present invention wherein the area of the boluses passing through the cuff is calculated. As with the process of FIG. 3, the process of FIG. 4 may be written in a suitable programming language and executed by the microprocessor 107 during operation of the NIBP monitor 120. Whereas the embodiment described with regard to FIG. 3 calculates the minimum wait time $t_{return}$ based in part on the time at each cuff measurement, the present embodiment determines the minimum wait time $t_{return}$ t based on the number of heart cycles H at each cuff pressure. The number of heart cycles H is easily determined from the oscillations detected by the pressure transducer 104 of the NIBP monitor 120. In particular, the amount of blood that is accumulated at a distal end of a limb to which the cuff 101 is attached is the sum of boluses of blood that squeeze through the artery under the cuff 101. The volume of the bolus is based on the difference of systolic pressure and cuff pressure. Thus, the volume of each bolus will be zero when the cuff pressure is greater than the systolic pressure, and the volume of each bolus will increase with decreasing cuff pressure. Based on this relationship, it can be appreciated by those of ordinary skill in the art that a matrix of cuff pressure CP versus heart cycles H can be constructed to determine the number of heart cycles H needed for safe venous return of accumulated blood.

Referring now to FIG. 4, at step 400 the process to determine a minimum wait period $t_{return}$ begins. At step 402 the area $\Delta A$ between the systolic pressure curve and the cuff pressure and the row counter i of the pressure/heart cycle table are initialized by setting $\Delta A$ to zero and i to 1. At step 404, it is determined if the current cuff pressure $CP_i$ is less than the systolic pressure SP (e.g., at time $t_1$ and $t_4$ in FIG. 2). If the $CP_i$ is less than the systolic pressure SP, then at step 406 the running total area ΔA of the systolic pressure curve minus cuff pressure curve is updated according to:

$$\Delta A_{i+1} = 66 A_i + ((SP-CP_i-15)*H)$$

where:
 ΔA$_i$=Total area under pressure-time curve at time i;
 SP=patient's systolic pressure;
 $CP_i$=cuff pressure at the pressure step at time i; and
 H=number of heart cycles.

The above relationship is illustrated by the exemplary graph 204 in FIG. 2. Although the above relationship utilizes heart cycles, as shown by the graph 204, a number of heart cycles may be correlated to time. The process continues at step 408 where the row counter i is incremented by one if it is determined at step 404 that the current cuff pressure $CP_i$ is not less than the systolic pressure SP, or upon the completion of step 406. At step 410 the row counter i is compared to an integer value n which represents the number of rows in the pressure/heart cycle table to determine if i is equal to n. As can be readily appreciated, the value of n will determine the number of step deflations of the cuff 101 performed by the NIBP monitor 120 for the particular cycle. If i is not equal to n, then the process returns to step 404. If i is equal to n, then at step 412 ΔA/k is calculated as in the FIG. 3 embodiment, and it is determined if ΔA/k is greater than 2 seconds, where k is the clinical constant determined as noted above. If at step 412 it is determined that ΔA/k is greater than 2 seconds, then the minimum wait time $t_{return}$ is set to the result of if ΔA/k at step 416. If at step 412 ΔA/k is not greater than 2 seconds, then the minimum wait time $t_{return}$ is set to a predetermined minimum wait time, e.g., 2 seconds, at step 414. After the wait time $t_{return}$ is determined either at step 414 or 416, the process for the current measurement cycle completes at step 418.

Thus, the present invention provides for a novel apparatus and method for determining a minimum wait period between successive blood pressure measurement cycles. As noted above, and in accordance with the first embodiment of the present invention, the pressure versus time curve for the previous inflation is utilized to determine the minimum wait time $t_{return}$, thus providing an adaptive rest time. The area under the pressure versus time curve is easily calculated and provides a good measure of patient discomfort because it is a measure of duration and applied pressure. Further, the method of adjusting the wait time $t_{return}$ in proportion to the area A provides for the appropriate time for patient recovery from the discomfort of the cuff pressure, and maximizes the amount of data made available to the clinician. In accordance with the second embodiment of the present invention, the volume of accumulated blood is determined based on a number of heart cycles and cuff pressure to determine the minimum wait time $t_{return}$ for safe venous return and to maximize patient comfort.

It will be appreciated by those skilled in the art that the foregoing has set forth the presently preferred embodiment of the invention and an illustrative embodiment of the invention but that numerous alternative embodiments are possible without departing from the novel teachings of the invention. For example, those skilled in the art will appreciate that the techniques of the invention may be used for blood pressure monitors in which the pressure is incremented from diastolic pressure as described, for example, in U.S. Pat. No. 4,461,266 to Hood et al. Also, those skilled in the art will appreciate that the techniques of the invention may be used for blood pressure monitors which do not use the amplitude matching techniques described by Ramsey to determine whether oscillation complexes of sufficient quality have been received. In addition, those skilled in the art will appreciate that shape of the oscillation complexes may also be determined by accumulating the average of the second derivative from the peak of an oscillation complex to the end of the diastolic phase of the oscillation complex. Accordingly, all such modifications are intended to be included within the scope of the appended claims.

What is claimed:

1. An automated sphygmomanometer apparatus, comprising:
 an inflatable pressure cuff;
 means for inflating said cuff to pressurize said cuff to a predetermined maximum pressure;
 means for sensing cuff pressure and for producing a cuff pressure determination signal representative of a sensed cuff pressure;
 means for selectively deflating said cuff to relieve pressure within said cuff; and
 means for controlling inflation/deflation cycles of said cuff in accordance with said cuff pressure determination signal by determining a minimum wait time between the end of a first inflation/deflation cycle and the beginning of a second inflation/deflation cycle in accordance with an area under an oscillometric envelope of the first inflation/deflation cycle divided by a clinical constant, where the end of the first inflation/deflation cycle is the point in time at which said deflating means deflates said cuff to a pressure below a predetermined minimum pressure.

2. The apparatus as recited in claim 1, wherein if said determined minimum wait time is less than a predetermined value, said controlling means sets said minimum wait time to a predetermined minimum wait time.

3. The apparatus as recited in claim 1, wherein said controlling means determines said area under said oscillometric envelope of the first inflation/deflation cycle by reading a first cuff pressure from the first inflation/deflation cycle that is greater than said predetermined minimum pressure and establishes a running total area under the oscillometric envelope by multiplying the difference between said first cuff pressure and said predetermined minimum pressure by a time at said first cuff pressure, and
 wherein said controlling means updates said running total area by reading subsequent cuff pressures from the first inflation/deflation cycle that are greater than said predetermined minimum pressure and recalculates the total area under the oscillometric envelope by multiplying the difference between each subsequent cuff pressure and said predetermined minimum pressure by a time at each subsequent cuff pressure and adding the result to said running total area.

4. The apparatus as recited in claim 3, wherein if said determined minimum wait time is less than a predetermined value, said controlling means sets said minimum wait time to a predetermined minimum wait time.

5. The apparatus as recited in claim 3, wherein once said controlling means determines that one of said subsequent cuff pressures is less than said predetermined minimum pressure, said controlling means determines said minimum wait time.

6. The apparatus as recited in claim 1, wherein said controlling means determines a systolic pressure from said oscillometric envelope and a curve of a difference between said systolic pressure and a cuff pressure versus a number of heart cycles at each pressure step, and determines said minimum wait time by dividing an area under said curve of said difference between said systolic pressure and said cuff pressure versus said number of heart cycles by said clinical constant.

7. The apparatus as recited in claim 6, wherein once said controlling means determines that one of said subsequent cuff pressures is less than said predetermined minimum pressure, said controlling means determines said minimum wait time.

8. The apparatus as recited in claim 6, wherein if said determined minimum wait time is less than a predetermined value, said controlling means sets said minimum wait time to a predetermined minimum wait time.

9. The apparatus as recited in claim 6, wherein said controlling means determines said area under said curve of said difference between said systolic pressure and said cuff pressure versus said number of heart cycles of the first inflation/deflation cycle by reading a first cuff pressure from the first inflation/deflation cycle that is less than said systolic pressure and establishes a running total area under said curve of said difference between said systolic pressure and said cuff pressure versus said number of heart cycles by multiplying the difference between said systolic pressure, said first cuff pressure and said predetermined minimum pressure by a number of heart cycles at said first cuff pressure, and wherein said controlling means updates said running total area by reading a predetermined number of subsequent cuff pressures from the first inflation/deflation cycle and recalculating the total area under said curve of said difference between said systolic pressure and said cuff pressure versus said number of heart cycles by multiplying the difference between said systolic pressure, each subsequent cuff pressure and said predetermined minimum pressure by a number of heart cycles at each subsequent cuff pressure and adding the result to said running total area.

10. The apparatus as recited in claim 9, wherein once said controlling means has read said predetermined number of subsequent cuff pressures, said controlling means determines said minimum wait time.

11. An automatic oscillometric blood pressure monitor comprising:

an inflatable pressure cuff;

means for inflating and deflating said cuff;

means for measuring cuff pressure and arterial pressure oscillation complexes through measurement of time varying cuff pressures within said cuff;

means for cyclically determining a patient's blood pressure at predetermined steps by instructing said inflating and deflating means to inflate said cuff about an artery of the patient until said cuff is at a pressure level above an estimated systolic pressure and to deflate said cuff by predetermined pressure steps, and for developing parameters representative of cuff pressure at each pressure step so as to form an oscillometric envelope of the patient; and means for determining a minimum wait time between the end of a first inflation/deflation cycle and the beginning of a second inflation/deflation in accordance with an area under said oscillometric envelope of the first inflation/deflation cycle of the patient divided by a clinical constant, where the end of the first inflation/deflation cycle is the point in time at which said cuff is deflated to a pressure below a predetermined minimum pressure.

12. The monitor as recited in claim 11, wherein if said determined wait time is less than a predetermined minimum value, said minimum wait time determining means sets said minimum wait time to a predetermined minimum wait time.

13. The monitor as recited in claim 11, wherein said minimum wait time determining means determines said area under said oscillometric envelope of the first inflation/deflation cycle by reading a first cuff pressure from the first inflation/deflation cycle that is greater than said predetermined minimum pressure and establishes a running total area under the oscillometric envelope by multiplying the difference between said first cuff pressure and said predetermined minimum pressure by a time at said first cuff pressure, and wherein said minimum wait time determining means updates said running total area by reading subsequent cuff pressures from the first inflation/deflation cycle that are greater than said predetermined minimum pressure and recalculates the total area under the oscillometric envelope by multiplying the difference between each subsequent cuff pressure and said predetermined minimum pressure by a time at each subsequent cuff pressure and adding the result to said running total area.

14. The monitor as recited in claim 13, wherein once said means for cyclically determining a patient's blood pressure determines that one of said subsequent cuff pressures is less than said predetermined minimum pressure, said minimum wait time determining means determines said minimum wait time.

15. The apparatus as recited in claim 13, wherein if said determined wait time is less than a predetermined value, said minimum wait time determining means sets said minimum wait time to a predetermined minimum wait time.

16. The monitor as recited in claim 11, wherein said minimum wait time determining means determines said minimum wait time by calculating an area under a curve formed by the difference of systolic pressure and cuff pressure at each pressure step versus a number of heart cycles, and dividing said area by said clinical constant.

17. The monitor as recited in claim 16, wherein once said means for cyclically determining a patient's blood pressure determines that one of said subsequent cuff pressures is less than said predetermined minimum pressure, said minimum wait time determining means determines said minimum wait time.

18. The apparatus as recited in claim 16, wherein if said determined wait time is less than a predetermined value, said minimum wait time determining means sets said minimum wait time to a predetermined minimum wait time.

19. The monitor as recited in claim 16, wherein said minimum wait time determining means determines said area under said curve of said difference between said systolic pressure and said cuff pressure versus said number of heart cycles of the first inflation/deflation cycle by reading a first cuff pressure from the first inflation/deflation cycle that is less than said systolic pressure and establishes a running total area under said curve of said difference between said systolic pressure and said cuff pressure versus said number of heart cycles by multiplying the difference between said systolic pressure, said first cuff pressure and said predetermined minimum pressure by a number of heart cycles at said first cuff pressure, and wherein said minimum wait time determining means updates said running total area by reading a predetermined number of subsequent cuff pressures from the first inflation/deflation cycle and recalculating the total area under said curve of said difference between said systolic pressure and said cuff pressure versus said number of heart cycles by multiplying the difference between said systolic pressure, each subsequent cuff pressure and said predetermined minimum pressure by a number of heart cycles at each subsequent cuff pressure and adding the result to said running total area.

20. The apparatus as recited in claim 19, wherein once said means for cyclically determining said patient's blood pressure has read said predetermined number of subsequent cuff pressures, said minimum wait time determining means determines said minimum wait time.

21. A method of monitoring blood pressure of a patient using an automated sphygmomanometer apparatus having an inflatable pressure cuff, said method comprising the steps of:
   inflating said cuff to pressurize said inflatable cuff to a pressure above an estimated systolic pressure of the patient;
   selectively deflating said cuff to relieve pressure within said cuff and producing cuff pressure determining signals at respective pressure levels;
   storing said cuff pressure determining signals at said respective pressure levels so as to form an oscillometric envelope;
   determining an area under said oscillometric envelope; and
   determining a minimum wait time between inflation/deflation cycles of said automated sphygmomanometer based on said area under said oscillometric envelope divided by a clinical constant.

22. The method as recited in claim 21, further comprising the steps of comparing said determined minimum wait time with a predetermined minimum wait time, and if said determined minimum wait time is less than said predetermined minimum wait time, setting said determined minimum wait time to said predetermined minimum wait time.

23. The method as recited in claim 21, further comprising the steps of:
   sensing blood pressure oscillations in said cuff pressure;
   producing an output representative of said blood pressure oscillations;
   determining a systolic pressure of the patient being monitored based on said output;
   determining data points representative of a curve corresponding to systolic pressure minus cuff pressure versus a number of heart cycles; and
   determining an area under said curve corresponding to systolic pressure minus cuff pressure versus a number of heart cycles,
   wherein said step of determining a minimum wait time comprises dividing said area under said curve corresponding to systolic pressure minus cuff pressure versus a number of heart cycles by said clinical constant.

24. The method as recited in claim 23, further comprising the step of comparing said determined minimum wait time with a predetermined minimum wait time, and if said determined minimum wait time is less than said predetermined minimum wait time, and setting said determined minimum wait time to said predetermine minimum wait time.

25. An automated sphygmomanometer apparatus, comprising:
   an inflatable pressure cuff;
   a source of pressurized air;
   an inflation valve which controls the inflation of said cuff to pressurize said inflatable cuff to a pressure above a patient's estimated systolic pressure;
   a pressure transducer which senses cuff pressure and produces a cuff pressure determination signal representative of a sensed cuff pressure;
   a deflation valve which selectively deflates said cuff to relieve pressure within said cuff; and
   a controller which controls the inflation/deflation cycles of said cuff in accordance with said cuff pressure determination signal by determining a minimum wait time between the end of a first inflation/deflation cycle and the beginning of a second inflation/deflation cycle in accordance with an area under an oscillometric envelope of the first inflation/deflation cycle divided by a clinical constant, where the end of the first inflation/deflation cycle is the point in time at which said deflation valve deflates said cuff to a pressure below a predetermined minimum pressure.

26. The apparatus as recited in claim 25, wherein if said determined minimum wait time is less than a predetermined value, said controller sets said minimum wait time to a predetermined minimum wait time.

27. The apparatus as recited in claim 25, wherein said controller determines said area under said oscillometric envelope of the first inflation/deflation cycle by reading a first cuff pressure from the first inflation/deflation cycle that is greater than said predetermined minimum pressure and establishes a running total area under the oscillometric envelope by multiplying the difference between said first cuff pressure and said predetermined minimum pressure by a time at said first cuff pressure, and
   wherein said controller updates said running total area by reading subsequent cuff pressures from the first inflation/deflation cycle that are greater than said predetermined minimum pressure and recalculates the total area under the oscillometric envelope by multiplying the difference between each subsequent cuff pressure and said predetermined minimum pressure by a time at each subsequent cuff pressure and adding the result to said running total area.

28. The apparatus as recited in claim 27, wherein once said controller determines that one of said subsequent cuff pressures is less than said predetermined minimum pressure, said controller determines said minimum wait time.

29. The apparatus as recited in claim 27, wherein if said determined minimum wait time is less than a predetermined value, said controller sets said minimum wait time to a predetermined minimum wait time.

30. The apparatus as recited in claim 25, wherein said controller determines a systolic pressure from said oscillometric envelope and a curve of a difference between said systolic pressure and a cuff pressure versus a number of heart cycles at each pressure step, and determines said minimum wait time by dividing an area under said curve of said difference between said systolic pressure and said cuff pressure versus said number of heart cycles by said clinical constant.

31. The apparatus as recited in claim 30, wherein once said controller determines that one of said subsequent cuff pressures is less than said predetermined minimum pressure, said controller determines said minimum wait time.

32. The apparatus as recited in claim 30, wherein if said determined minimum wait time is less than a predetermined value, said controller sets said minimum wait time to a predetermined minimum wait time.

33. The apparatus as recited in claim 30, wherein said controller determines said area under said curve of said difference between said systolic pressure and said cuff pressure versus said number of heart cycles of the first inflation/deflation cycle by reading a first cuff pressure from the first inflation/deflation cycle that is less than said systolic pressure and establishes a running total area under said curve of said difference between said systolic pressure and said cuff pressure versus said number of heart cycles by multiplying the difference between said systolic pressure, said first cuff pressure and said predetermined minimum pressure by a number of heart cycles at said first cuff pressure, and wherein said controller updates said running total area by reading a predetermined number of subsequent cuff pressures from the first inflation/deflation cycle and recalculating the total area under said curve of said difference between said systolic pressure and said cuff pressure versus said number of heart cycles by multiplying the difference between said systolic pressure, each subsequent cuff pressure and said predetermined minimum pressure by a number of heart cycles at each subsequent cuff pressure and adding the result to said running total area.

34. The apparatus as recited in claim 33, wherein once said controller has read said predetermined number of subsequent cuff pressures, said controller determines said minimum wait time.

* * * * *

UNITED STATES PATENT AND TRADEMARK OFFICE
CERTIFICATE OF CORRECTION

PATENT NO. : 5,993,396
DATED : November 30, 1999
INVENTOR(S) : Friedman et al.

It is certified that error appears in the above-identified patent and that said Letters Patent is hereby corrected as shown below:

Col. 3, line 40, change "1/50" to --1/5--;

Col. 9, line 5, in the equation change "66" to --Δ--;

Col. 13, line 62, "predetermine" should be --predetermined--.

Signed and Sealed this

Twenty-eighth Day of November, 2000

Attest:

Q. TODD DICKINSON

Attesting Officer

Director of Patents and Trademarks